United States Patent [19]

Lin et al.

[11] Patent Number: 4,816,589
[45] Date of Patent: Mar. 28, 1989

[54] AMINOPROPYLIMIDAZOLES

[75] Inventors: Shiow-Ching Lin, Ellicott City; Jennifer M. Quirk, Highland, both of Md.

[73] Assignee: W. R. Grace & Co.-Conn., New York, N.Y.

[21] Appl. No.: 82,179

[22] Filed: Aug. 6, 1987

[51] Int. Cl.$^4$ .......................................... C07D 233/58
[52] U.S. Cl. ................................................. 548/341
[58] Field of Search ...................................... 548/341

[56] References Cited

U.S. PATENT DOCUMENTS 4,710,571 12/1987 Hofman et al. .................. 548/341

OTHER PUBLICATIONS

Hugo Bauer, Hydrogenation of the Imidazole Ring, J. Org. Chem. 26, 1649 (1961).
M. R. Grimmett, Adv. Imidazole Chem., 1970, 12, 161.
March, J. Adv. Org. Chem., 3rd Ed., 1093 (1985).
Rylander, Cat. Hydrog. in Org. Synth., 226 (1979).

*Primary Examiner*—Mary C. Lee
*Assistant Examiner*—J. Richter
*Attorney, Agent, or Firm*—Charles A. Cross; W. W. McDowell, Jr.

[57] ABSTRACT

1-Cyanoethylimidazoles are hydrogenated to provide the correspondng 1-aminopropylimidazoles, e.g., an ethanol solution of 1-cyanoethyl-2-ethyl-4-methylimidazole is hydrogenated at 1000 psi using Raney nickel catalyst to prepare 1-aminpropyl-2-ethyl-4-methylimidazole, useful as an intermediate in the preparation of epoxy accelerators.

5 Claims, No Drawings

AMINOPROPYLIMIDAZOLES

RELATED APPLICATION

U.S. Ser. No. 082,168 filed Aug. 6, 1987 (Docket 7057), "Fastcuring Agents and Accelerators for Epoxy Resins," inventors Shiow Ching Lin and Ping-Lin Kuo, discloses the use of aminopropylimidazole/isocyanate adducts as accelerators for epoxy resins.

The instant invention is directed to the synthesis of aminopropylimidazoles of the structure:

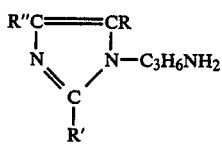

where R, R' and R" are independently H or alkyl or 1-6 carbons.

These aminopropylimidazoles can be prepared by hydrogenation of the corresponding source cyanoethylimidazole, thus:

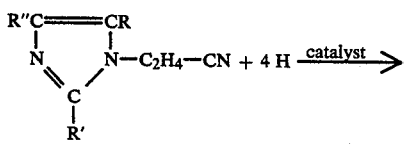

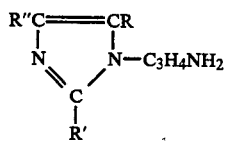

where R, R', and R" have the above meanings.

Reduction of the cyano- group exclusively in a cyanoalkylimidazole was not to be expected. According to the literature, other reactions were more likely. There were two major concerns: 1) hydrogenation of one or both of the double bonds in the imidazole ring; and 2) fragmentation of the cyanoalkyl side chain. As to 1), unsubstituted imidazole has aromatic unsaturation and is reduced with difficulty, and/or with addition of substituents to the ring. For example, hydrogenation of imidazole in acetic anhydride solvent with platinum oxide catalyst results in both reduction and acetylation, with formation, e.g., of diacetylimidazolidine. J. Org. Chem. 26, 1649 (1961). However, a substituted imidazole loses its aromatic character and behaves more like a conjugated diene. Such olefinic unsaturation is readily hydrogenated. For example, reduction of 2-methyl-4,5-diphenylimidazole across the 4,5-double bond has been reported; M. R. Grimmett, Adv. Imidazole Chem., 1970, 12, 161. Indeed, olefinic hydrogenation would be expected to occur well before -CN reduction. (March, Advanced Organic Chemistry, 3rd Ed., p. 1093.) However, so far as we can determine, the imidazole ring, though substituted, is unaffected by our process. Only the -CN group is reduced.

As for 2), fragmentation of the side chain, this is reported by Rylander, Catalytic Hydrogenation in Organic Syntheses, Academic Press, p. 226 (1979); viz., attempted hydrogenation of 4-(benzylmethylaminomethyl)imidazole in methanol containing HCl over 5% palladium-on-carbon split off the benzyl group. That is to say, the side chain was split by hydrogenolysis. We note no such side chain destruction in our process.

EXAMPLE 1

1-Aminopropyl-2-ethyl-4-methyl-imidazole

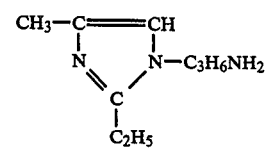

1 g 1-cyanoethyl-2-ethyl-4-methylimidazole was put in 20 ml of ethanol into a high-pressure reactor. Raney nickel (50 mg) was added as the catalyst, and the reactor was pressured to 1000 psi with hydrogen and heated to 100° C. for 18 hours. The reactor was cooled down and the excess hydrogen was vented. The product was identified as 1-aminopropyl-2-ethyl-4-methylimidazole by gas chromatography and mass spectra.

Substantially identical results were obtained when other catalysts were used instead of Raney nickel, viz., Example 2, palladium-on-carbon; and Example 3, rhodium-on-carbon. Other useful catalysts include, Raney cobalt, palladium-on-alumina, platinum-on-carbon, platinum-on-alumina, ruthenium-on-carbon, ruthenium-on-alumina, ruthenium dichloride triphenylphosphine, rhodium-on-alumina, rhodium chloride triphenylphosphine, iridium-on-carbon, iridium-on-alumina, and the like.

1-Cyanoethyl-2-ethyl-4-methyl-imidazole is available commercially and can be made by reacting 2-ethyl-4-methyl-imidazole with acrylonitrile.

The hydrogenation conditions can be varied considerably. The hydrogen pressure can range from 50 to 2000 psi, the reaction temperature from room temperature (about 20° C) to 150° C., and the reaction time from 15 (minutes to 24 hours. Within these ranges the milder conditions are preferred, e.g., 500 to 1000 psi, at 50° to (100° C., for 2 to 18 hours.

Use

A major use of the products of this invention is in the preparation of accelerators/curing agents for epoxy resin systems, as described below.

The following is summarized from the above-referenced copending U.S. Ser. No. 082,168 filed 8/6/87, Lin et al.

EXAMPLE 4

With vigorous stirring 35 g of toluenediisocyanate was added to an aqueous solution containing 55 g of 1-aminopropyl-2-ethyl-4-methyl-imidazole and 100 ml of water. After completion of the addition the solution was stirred further for 2 hours. A white precipitate of the imidazole-isocyanate adduct was formed. It was filtered, washed with water, and dried at room temperature, after which it was pulverized to a fine powder.

EXAMPLE 5

The adduct of the preceding Example (3.4 parts by weight) was uniformly blended with an epoxy resin containing 100 parts of an epoxy resin made from diglycidyl ether and Bisphenol A (available commercially as Epon 828 from Shell Chemical Company) and 6 parts of dicyandiamide to form a one-package epoxy system.

The blend was stored in an oven at 40° C.for 10 days. No noticeable viscosity change was observed. The fresh one-package epoxy system was curable at 170° C.in 6 seconds.

1-Aminopropyl-2-methyl-imidazole, 1-aminopropylimidazole, and 1-aminopropyl-2-ethyl-imidazole were also prepared from the respective cyanoethylimidazoles, following the procedure of Example 1.

We claim:

1. Aminopropylimidazole of the structure

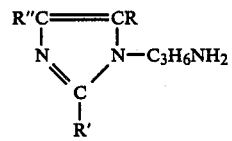

where R, R', and R" are independently selected from the group consisting of H and alkyl of 1-6 carbons.

2. An aminopropylimidazole according to claim 1, wherein R is hydrogen, R' is ethyl and R" is methyl.

3. An aminopropylimidazole according to claim 1, wherein R is hydrogen, R' is methyl and R" is hydrogen.

4. An aminopropylimidazole according to claim 1, wherein R is hydrogen, R' is ethyl and R" is hydrogen.

5. An aminopropylimidazole according to claim 1, wherein R, R' and R" are hydrogens.

* * * * *